(12) United States Patent
Yamada et al.

(10) Patent No.: US 6,852,970 B2
(45) Date of Patent: Feb. 8, 2005

(54) MASS SPECTROMETER

(75) Inventors: Masuyoshi Yamada, Ichikawa (JP); Izumi Waki, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 10/699,805

(22) Filed: Nov. 4, 2003

(65) Prior Publication Data

US 2004/0104342 A1 Jun. 3, 2004

(30) Foreign Application Priority Data

Nov. 8, 2002 (JP) ........................................ 2002-324684

(51) Int. Cl.[7] .............................................. H01J 49/28
(52) U.S. Cl. ....................... 250/288; 250/281; 250/282; 250/423 R
(58) Field of Search ............................ 250/288, 423 R, 250/281, 282

(56) References Cited

U.S. PATENT DOCUMENTS 5,969,351 A * 10/1999 Nabeshima et al. ........ 250/288
6,462,336 B1 * 10/2002 Bajic .......................... 250/288
2003/0122069 A1 * 7/2003 Kato

FOREIGN PATENT DOCUMENTS

JP             6-310091        4/1993

* cited by examiner

Primary Examiner—John R. Lee
Assistant Examiner—Zia R. Hashmi
(74) Attorney, Agent, or Firm—Reed Smith LLP; Stanley P. Fisher, Esq.; Juan Carlos A. Marquez, Esq.

(57) ABSTRACT

There will be provided a mass spectrometer for detecting impurity in sample gas of a low flow rate. A mass spectrometer including: an atmospheric pressure chemical ionization source having a primary ionization part 28 for generating a primary ion by means of electric discharge of reagent gas, and a secondary ionization part 23 for generating an ion of the sample by a reaction of the primary ion and the sample; a mass spectrometric part 11 for performing mass spectrometric analysis of the ion generated; a mixing portion 33 for mixing the sample to be introduced into the secondary ionization part with dilution gas; and a mean 30 for controlling a flow rate of the dilution gas for flowing through the mixing portion; and a mean 12-1 or 12-2 or 12-3 for controlling a flow rate of the sample gas, wherein mixed gas obtained by mixing the sample with the dilution gas is introduced into the secondary ionization part and the sample is ionized.

11 Claims, 6 Drawing Sheets

ONLINE ANALYSIS

MASS SPECTROMETER

BACKGROUND OF THE INVENTION

The present invention relates to a mass spectrometer which detects impurity in sample gas of a low flow rate in a high sensitivity by atmospheric pressure chemical ionization.

There is known a gas analytical device using GC-PID (Gas chromatography-photo-ionization detection), or a sector type mass spectrometer using a magnetic field. Also, there is known a semiconductor sensor for detecting hydrogen.

An APCI-MS (Atmospheric Pressure Chemical Ionization Mass Spectrometer) is a device which selectively ionizes traces of components to be contained in a sample by taking advantage of an ion molecular reaction to detect in a high sensitivity, and has been used for biotechnology such as protein analysis and for impurity analysis in a semiconductor process.

In an analysis of gas which is prone to contaminate an ion source, a primary ionization part is separated from a sample inlet part, whereby clean gas is introduced into the primary ionization part to generate a primary ion; sample gas introduced into the sample inlet part is mixed with the primary ion generated in the primary ionization part to ionize an object substance to be contained in the sample gas by an ion-molecule reaction (See Japanese Patent Application Laid-Open No. 6-310091).

There has been requested a technique by which a sample is sampled from a system targeted for inspection without disturbing the system targeted for inspection as far as possible and the system targeted for inspection is inspected in a state in which the target of inspection is maintained in a dynamic state.

For example, in development of a fuel cell, in order to investigate mass balance of gas at inlet and outlet of the fuel cell for evaluating the power generation efficiency, it has become an important problem to confirm how the efficiency changes by changing parameters for temperature, flow rate and the like. In order to evaluate performance of the fuel cell, there has been increasing a request for measuring analysis of gas components at inlet and outlet of the fuel cell online.

In order to evaluate the performance of the fuel cell, highly-sensitive detectability on the order of ppm is requested. Detection sensitivity of hydrogen by a semiconductor sensor is on the order of 0.1% to 1%, and is insufficient in sensitivity. In an analysis due to GC-PID, since a separation process by GC is required, data can be obtained only at intervals of-several minutes at a minimum even if online type GC is used, and a transient operation of the fuel cell cannot be evaluated.

There has been known a sector type mass spectrometer using a magnetic field capable of continuously analyzing hydrogen concentration of the fuel cell in real time, the sensitivity is generally on the order of 0.1%, and a sampling flow rate of about (3 to 4) L/min (liter/minute) is required.

A flow rate of each of hydrogen and air necessary for an operation of the fuel cell is generally about 1 L/min, and when a sampling flow rate during an online analysis is high, a flow rate of hydrogen and air during an ordinary operation becomes different from that of hydrogen and air during an online analysis. In other words, there is a problem that it becomes difficult to accurately evaluate performance of an operation system of the fuel cell and the fuel cell.

Also, in an EI-MS (Electron Impact Mass Spectrometer) in which ionization is performed in a vacuum, since a multiplicity of fragment ions obtained by decomposing an original ion are generated during ionization, it is difficult to specify an ion derived from hydrogen in gas sampled and to determine precise concentration.

In the conventional technique, no consideration has been given in sampling while the fuel cell is maintained in a normal operating state without disturbing a system targeted for inspection, for example, an operating system of the fuel cell.

SUMMARY OF THE INVENTION

It is an object of the present invention to provide a mass spectrometer which detects, in a high sensitivity, impurity in sample gas of a low flow rate, and to provide a mass spectrometer which analyzes samples without disturbing a system targeted for inspection as far as possible.

In a mass spectrometer according to the present invention, a substance targeted for measurement on the order of ppm in the sample is measured with as low a sampling flow rate as about 0.1 L/min.

In a mass spectrometer according to the present invention, there is used an atmospheric pressure chemical two-step ionization source composed of: a primary ionization part for generating primary ions by means of electric discharge of reagent gas (gas for generating a primary ion, argon or helium); and a secondary ionization part for generating secondary ions of a sample by a reaction of the primary ion and a sample to be introduced from a sample inlet. The primary ionization part is formed with an inlet for introducing reagent gas and an outlet for discharging gas for generating the primary ions. Between the primary ionization part and the secondary ionization part, there is arranged a counter electrode having a hole through which the primary ions are caused to pass through toward the secondary ionization part. The secondary ionization part is maintained at negative pressure as compared with the primary ionization part.

The ions generated in the secondary ionization part is introduced into a mass spectrometric part which has been evacuated in a high vacuum, through an aperture, and mass spectrometric analysis is performed by a mass spectrometer such as a quadrupole type mass spectrometer, an ion trap type mass spectrometer, an ion trap-TOF type (time of flight type) mass spectrometer and a magnetic field type mass spectrometer.

A sample introduced from a target of inspection is mixed with dilution gas in a mixing portion, and is introduced into the secondary ionization part at a substantially constant flow rate (1 L/min). Flow rates of dilution gas and the sample which are to flow into the mixing portion are controlled by flow rate control means respectively. A flow rate of the dilution gas for flowing through the mixing portion is to be set higher than that of the sample for flowing through the mixing portion. For example, assuming that a flow rate of dilution gas for flowing through the mixing portion is 0.9 L/min or higher, a flow rate of the sample for flowing through the mixing portion is 0.1 L/min or lower, and that of gas mixed in the mixing portion is about 1 L/min, these will be introduced into the secondary ionization part.

As described above, the flow rate of the sample to be introduced from the target of inspection is reduced, whereby an influence on the target of inspection by the sampling can be reduced. In this respect, when an outlet flow rate of the reagent gas to the secondary ionization part is set within a range of (0.1 to 0.3) L/min, a suitable sensitivity can be obtained.

For the dilution gas, there will be selected dilution gas which does not interfere with ionization of a substance targeted for measurement in the sample. There will be used dilution gas, ionization potential of which is the same as or higher than ionization potential of the substance targeted for measurement, or dilution gas, proton affinity of which is the same as or lower than that of the substance targeted for measurement is used, whereby an influence of lowered concentration of the substance targeted for measurement due to mixing of the dilution gas can be mitigated even at low sampling flow rate without interfering with the ionization of the substance targeted for measurement.

When, for example, a polymer elecrolyte fuel cell is inspected, the sample is collected from an inlet piping for introducing gas or liquid to the fuel cell or an outlet piping for discharging gas or liquid from the fuel cell. A sample inlet of the secondary ionization part and the above-described inlet piping or outlet piping are connected together through a sample inlet piping through which the sample collected is to flow. To this sample inlet piping, there is connected a dilution gas piping through which the dilution gas flows. In the dilution gas piping, there is arranged flow rate control means for controlling the flow rate of the dilution gas, and in the sample inlet piping, there is arranged flow rate control means for controlling the flow rate of the sample collected. With such structure, the substance targeted for measurement in the sample collected can be analyzed online in real time. It goes without saying that the sample collected can be directly introduced into a sample inlet of the secondary ionization part for being analyzed without mixing with the dilution gas.

From a gas outlet piping on cathode of the polymer electrolyte fuel cell, sample gas is collected, traces of hydrogen in the sample gas is selectively ionized through the use of any of argon, helium and nitrogen as the dilution gas, and through the use of the atmospheric pressure chemical two-step ionization source, and traces of hydrogen can be measured in a high sensitivity online in real time.

DETAILED DESCRIPTION OF THE PREFERRED EMBODIMENTS

In the following description, as a system targeted for inspection, the polymer elecrolyte fuel cell will be exemplified for description.

Figure 3:
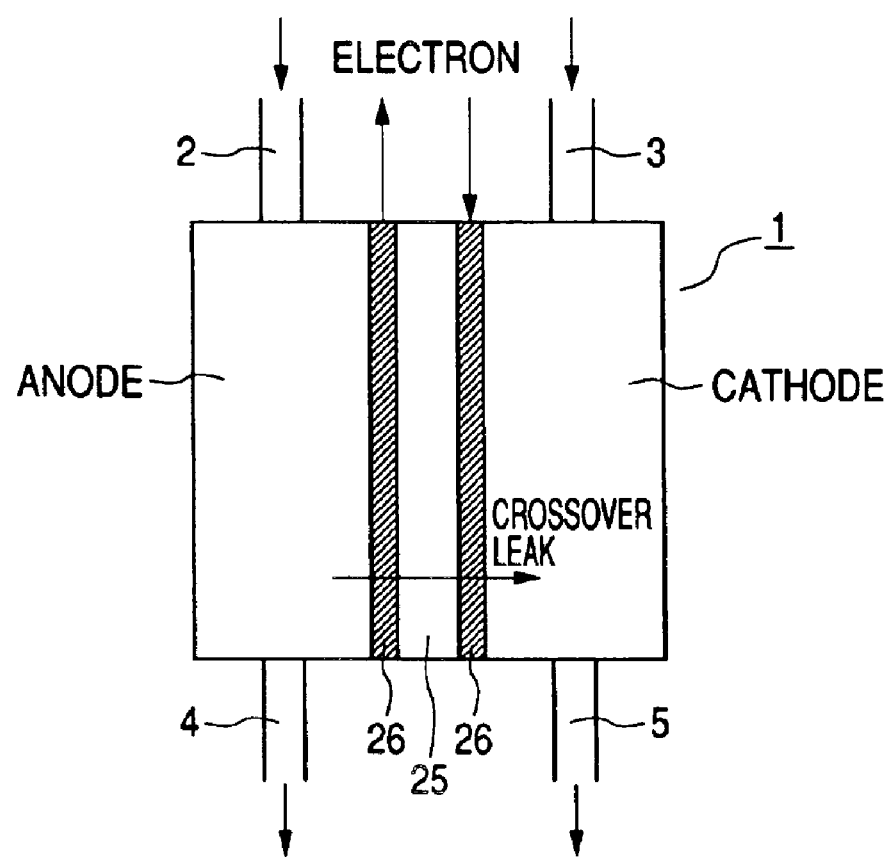
FIG. 3 is a view for explaining structure of a polymer electrolyte fuel cell to which the present invention is applied.

FIG. 3 is a view for explaining structure of a polymer electrolyte fuel cell to which the present invention is applied. As regards the polymer electrolyte fuel cell 1 (PEFC), the development has been pursued as an automotive and dispersal power source or as a fuel cell for a household. As shown in FIG. 3, hydrogen gas is introduced as fuel from a gas inlet piping 2 on anode of the fuel cell, is discharged from a gas outlet piping 4 on anode, air is introduced from a gas inlet piping 3 on cathode, and is discharged from a gas outlet piping 5 on cathode.

By a catalytic action of a polymer electrolyte membrane 25, a hydrogen molecule is dissociated by a hydrogen atom on anode, further emits electrons, proton ($H^+$) generated moves from an electrode 26 on anode to an electrode 26 on cathode, and reacts with an oxygen molecule in air to form water. At this time, an electric current flows between the electrode 26 on anode and the electrode 26 on cathode. In order to evaluate performance of the fuel cell online, it becomes necessary to measure concentration of hydrogen that flows through the gas inlet piping 2 on anode, and the gas outlet piping 4 on anode, and concentration of oxygen, nitrogen, and water content, and the like that flow through the gas inlet piping 3 on cathode and the gas outlet piping 4 on cathode.

In evaluation of performance of a polymer electrolyte membrane 25 of the fuel cell 1, it becomes important to measure an amount of crossover leak. The crossover leak is a phenomenon in which a hydrogen molecule introduced to the anode side moves within the membrane 25 toward the cathode side, for leaking on the cathode side in a state of hydrogen molecule instead of converting to proton by a catalytic action of a polymer electrolyte membrane 25, and permeating the interior of the membrane The hydrogen molecule that has leaked on the cathode side reacts vigorously with oxygen molecules in air on the cathode side of the membrane 25 to deteriorate the polymer electrolyte membrane 25 for increasing the amount of crossover leak more and more. Gradually, the electric power decreases and the fuel cell becomes unable to sufficiently perform.

The concentration (amount of crossover leak) of the hydrogen molecule that has leaked on the cathode side can be determined by measuring concentration of trace hydrogen in the gas for flowing through the gas outlet piping 5 on cathode. This amount of crossover leak is on several ppm level at least. For a device for evaluating online an operating performance in a state in which the fuel cell has been actuated, highly sensitive detectability on the order of ppm is required as described previously.

As a portable fuel cell the development of which has been pursued for a portable computer or a portable telephone, there is a Direct Methanol Fuel Cell (DMFC). In the DMFC, methanol is introduced on the anode side as fuel. Even in the case of performance evaluation of the DMFC, it is important to measure the crossover leak as in the case of the PEFC. In the DMFC, when there is crossover leak, methanol permeates on the cathode side and reacts with oxygen molecules vigorously to deteriorate the membrane.

Therefore, in measurement of the crossover leak of the DMFC, when measurement is performed in a state in which the fuel cell is not operated, inactive gas such as nitrogen and rare gas is introduced into the gas inlet piping 3 on cathode, and there is measured trace methanol to be contained in gas that flows through the gas outlet piping 5 on cathode that has leaked on the cathode side. When measurement is performed in a state in which the fuel cell is operated, the methanol that has permeated the membrane 25 is changed into $CO_2$ by the catalytic action of the membrane 25 on the cathode side, and therefore, there is measured trace $CO_2$ on the order of ppm to be contained in gas that flows through the gas outlet piping 5 on cathode.

Figure 1:
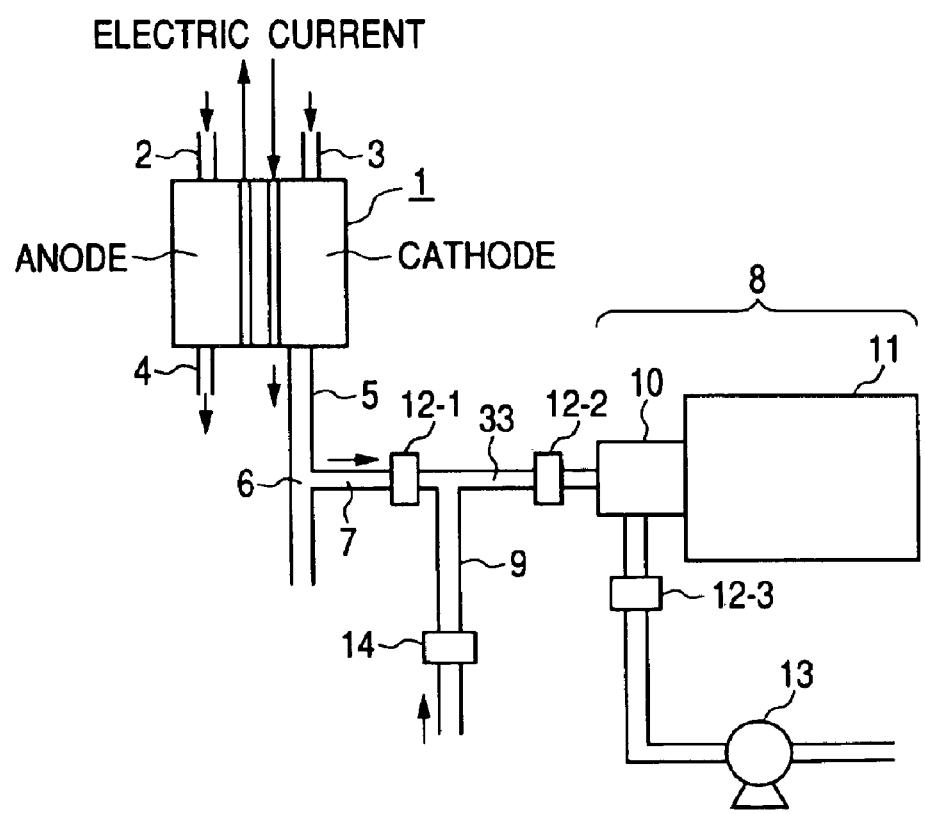
FIG. 1 shows an example of the present invention, and is a view explaining structure in which outlet gas of a fuel cell is analyzed online through the use of a mass spectrometer.

FIG. 1 shows an example of the present invention, and is a view explaining structure in which outlet gas of a fuel cell is analyzed online through the use of a mass spectrometer. As shown in FIG. 3, in a fuel cell 1, there are connected together a gas inlet piping 2 on anode for introducing hydrogen gas, a gas outlet piping 4 on anode for discharging hydrogen gas that has not been consumed, a gas inlet piping 3 on cathode for introducing air, and a gas outlet piping 5 on cathode for discharging air.

To a branch 6 of the gas outlet piping 5 on cathode, there is connected a sample gas inlet piping 7, and the sample gas inlet piping 7 is connected to a mass spectrometer 8. A dilution gas piping 9 in which a mass flow controller 14 has been arranged is connected to the sample gas inlet piping 7. The mass spectrometer 8 is composed of an ion source 10 and a mass spectrometric part 11 evacuated in a high vacuum.

A portion or the whole quantity of gas exhausted into the gas outlet piping 5 on cathode of the fuel cell 1 is sampled in order to measure a crossover leak of hydrogen. The gas thus sampled is (1) introduced into the mass spectrometer 8 as it is as sample gas, or (2) is mixed with dilution gas to be introduced into the sample gas inlet piping 7 from the dilution gas piping 9, and is introduced into the mass spectrometer as sample gas containing hydrogen as substance targeted for measurement.

The sample gas is introduced into the ion source 10 by a pump 13. At this time, in order to stabilize the sensitivity of the mass spectrometer, it is important to make an amount of inlet of the sample gas into the ion source 10 constant.

Figure 2:
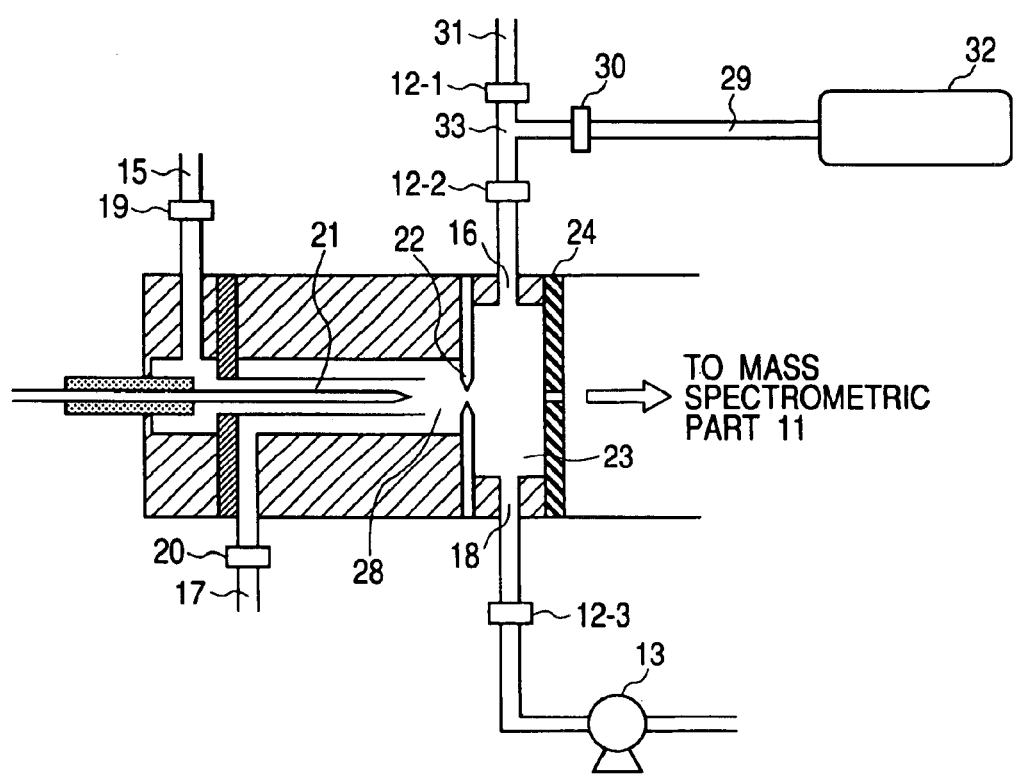
FIG. 2 is a view showing detailed structure of an ion source according to an example of the present invention, structure in which the sample is mixed with gas.

The flow rate of the sample gas is controlled by a mass flow controller to be arranged in any of the following (1), (2) and (3). (1) a mass flow controller 12-1 to be arranged in a sample gas inlet piping (in FIG. 1, piping indicated by 7, in FIG. 2, piping indicated by 31 through which the branch 6 of FIG. 1 is connected to the dilution gas inlet 16) between the branch 6 and a mixing portion 33 (will be described later). (2) a mass flow controller 12-2 to be arranged in a mixed gas inlet piping (in FIG. 1, piping indicated by 7, in FIG. 2, piping indicated by 31 through which the branch 6 of FIG. 1 is connected to the dilution gas inlet 16) between the mixing portion 33 and an ion source (although indicated by the secondary ionization part 23 in FIG. 2, indicated by the ion source 10 in FIG. 1). In other words, the mass flow controller 12-2 is, as shown in FIG. 2, arranged in the sample gas inlet piping between the mixing portion 33 and the dilution gas inlet 16. (3) A mass flow controller 12-3 to be arranged in the mixed gas outlet piping between the ion source (although indicated by the secondary ionization part 23 in FIG. 2, indicated by the ion source 10 in FIG. 1) and the pump 13. In other words, the mass flow controller 12-3 is, as shown in FIG. 2, arranged in the dilution gas outlet piping between the mixed gas outlet 18 and the pump 13.

The flow rate of sample gas that flows from the branch 6 of the gas outlet piping 5 on cathode to the sample gas inlet piping 7 is controlled by the mass flow controller 12-1 or 12-2 to be arranged in the sample gas inlet piping 7. When there is a high possibility that substance targeted for measurement contaminates the mass flow controller 12-1 or 12-2, the mass flow controller 12-3 can be provided in piping between the ion source 10 and the pump 13 for controlling.

As the ion source 10, there is used an atmospheric pressure chemical ionization source (APCI). The APCI is a method for chemically ionizing traces of molecules targeted for measurement in the sample from a primary ion generated in the atmosphere by an ion-molecule reaction, is advantageous in terms of selectivity and sensitivity, it is possible to perform soft ionization of a molecule targeted for measurement because of low ionization energy, and has a feature that it generates few fragment ions. For this reason, it is effective to determine a substance of a low mass number such as hydrogen. Particularly, a two-step ion source, in which the primary ionization part is separated from the secondary ionization part for performing the secondary ionization, is particularly effective to measure hydrogen.

FIG. 2 is a view showing detailed structure of an ion source 10 according to an example of the present invention, structure in which the sample is mixed with gas (dilution gas). As shown in FIG. 2, the ion source is composed of the primary ionization part 28 and the secondary ionization part 23 for performing the secondary ionization. The secondary ionization part is maintained at negative pressure as compared with the primary ionization part.

By means of the mass flow controller 12-1 or 12-2 to be arranged in the sample gas inlet piping 31 connected to the branch 6 shown in FIG. 1, or the mass flow controller 12-3 to be arranged in the mixed gas outlet piping between the mixed gas outlet 18 and the pump 13, there are mixed sample gas from the sample gas inlet piping 31, that has been controlled at a constant flow rate, and dilution gas from a dilution gas tank 32, that has been controlled at a constant flow rate by the mass flow controller 30 to be arranged in the dilution gas inlet piping 29 in a mixing portion 33 in which a sample gas inlet piping 31 and a dilution gas inlet piping 29 have been coupled with each other. Mixed sample gas obtained by mixing the sample gas with the dilution gas is introduced into the secondary ionization part 23 of the ion source from a mixed sample gas inlet 16.

As reagent gas, such as argon and helium, gas having higher ionization potential than ion which becomes an object of measurement or gas having lower proton affinity is introduced into the primary ionization part 28 from a reagent gas inlet piping 15. Here, the description will be made of a case where argon is used. Argon gas is ionized in the vicinity of a needle electrode 21 to which high voltage of several kV has been applied (Chemical Formula 1). In order to stabilize the ionization, it is important that an inlet amount of argon gas is controlled constant by a mass flow controller 19 arranged in the reagent gas inlet piping 15.

$Ar \rightarrow Ar^+$ (Chemical Formula 1)

Argon ions thus generated pass through a hole of a counter electrode 22 together with a portion of argon gas, and are introduced into the secondary ionization unit 23. The remaining argon gas is discharged through a reagent gas outlet piping 17, and in order to make a flow rate of argon gas to be introduced into the secondary ionization part 23 constant, the flow rate of the argon gas to be discharged is controlled constant by the mass flow controller 20 arranged in the reagent gas outlet piping 17.

In the secondary ionization part 23, the argon gas and the primary ions ($Ar^+$) are mixed with the sample gas to cause a secondary ionization reaction. When the sample gas containing hydrogen as a substance targeted for measurement is air or nitrogen, ion ($N_2H^+$) which becomes an object of measurement is generated by reactions (Chemical Formula 2), (Chemical Formula 3) as below.

$$Ar^+ + N_2 \rightarrow N_2^+ + Ar \quad \text{(Chemical Formula 2)}$$

$$N_2^+ + H_2 \rightarrow N_2H^+ + H \quad \text{(Chemical Formula 3)}$$

The ion $N_2H^+$ thus generated is introduced into a mass spectrometric part 11 evacuated in a high vacuum through the aperture 24 for mass spectrometric analysis. In order to increase an amount of ion $N_2H^+$ to be introduced into the mass spectrometric part, there are provided electrical potential gradients in the order of the needle electrode 21, the counter electrode 22 and the aperture 24, and the ion is drawn into the aperture 24 according to the electrical potential difference.

Gas mixed in the secondary ionization part 23 is partially introduced into the aperture 24 due to a pressure difference, and the rest is exhausted through the mixed gas outlet 18. As described above, even in the flow rate of the sample gas, it is important to control constant by the mass flow controller 12-1 or 12-2, or to control the flow rate of the dilution gas constant by the mass flow controller 12-3 installed on the exhaust side for exhausting the dilution gas from the dilution gas outlet 18.

A flow rate of sample necessary for the atmospheric pressure chemical ion source is about 1 L/min. As described above, a flow rate of gas to be consumed in an online analysis using the mass spectrometer is preferably as low as possible in order not to disturb an operating system of the fuel cell.

As shown in FIG. 2, dilution gas is introduced into the sample gas inlet piping 31 from the dilution gas piping 29. As the dilution gas, such gas having low proton affinity as not to disturb the reaction of (Chemical Formula 3), for example, argon, helium or nitrogen itself is also effective. Since ionization due to the reaction of (Chemical Formula 3) is not interfered because of the existence of the dilution gas even if such dilution gas is mixed with the sample gas, it is possible to mitigate an influence of lowered concentration of the substance targeted for measurement due to mixing of the dilution gas.

The maximum effect of mixing the dilution gas with the gas sampled is to be able to reduce a flow rate of gas to be sampled from the fuel cell. For a flow rate necessary for gas for flowing into the atmospheric pressure chemical ionization source, about 1 L/min will suffice. Therefore, since for total gas flow rate after the sampled gas is mixed with the dilution gas, about 1 L/min will suffice, if, for example, the flow rate of the dilution gas is assumed to be 0.9 L/min, for the flow rate of gas to be sampled from the fuel cell, 0.1 L/min will suffice, and it becomes possible to perform online analysis without disturbing the system of fuel cell. In other words, the flow rate of gas to be sampled from gas exhausted to the gas outlet piping 5 on cathode of the fuel cell 1 is reduced as far as possible, whereby it is possible not to affect the flow rate of gas for flowing on the anode and cathode sides as far as possible.

As a mass spectrometer for use with the mass spectrometric part 11, there is applicable a mass spectrometer such as a quadrupole type mass spectrometer, an ion trap type mass spectrometer, an ion trap-TOF type mass spectrometer and a magnetic field type mass-spectrometer. Hereinafter, the description will be made of an example of result in which measurement has been made using the quadrupole type mass spectrometer.

Figure 4:
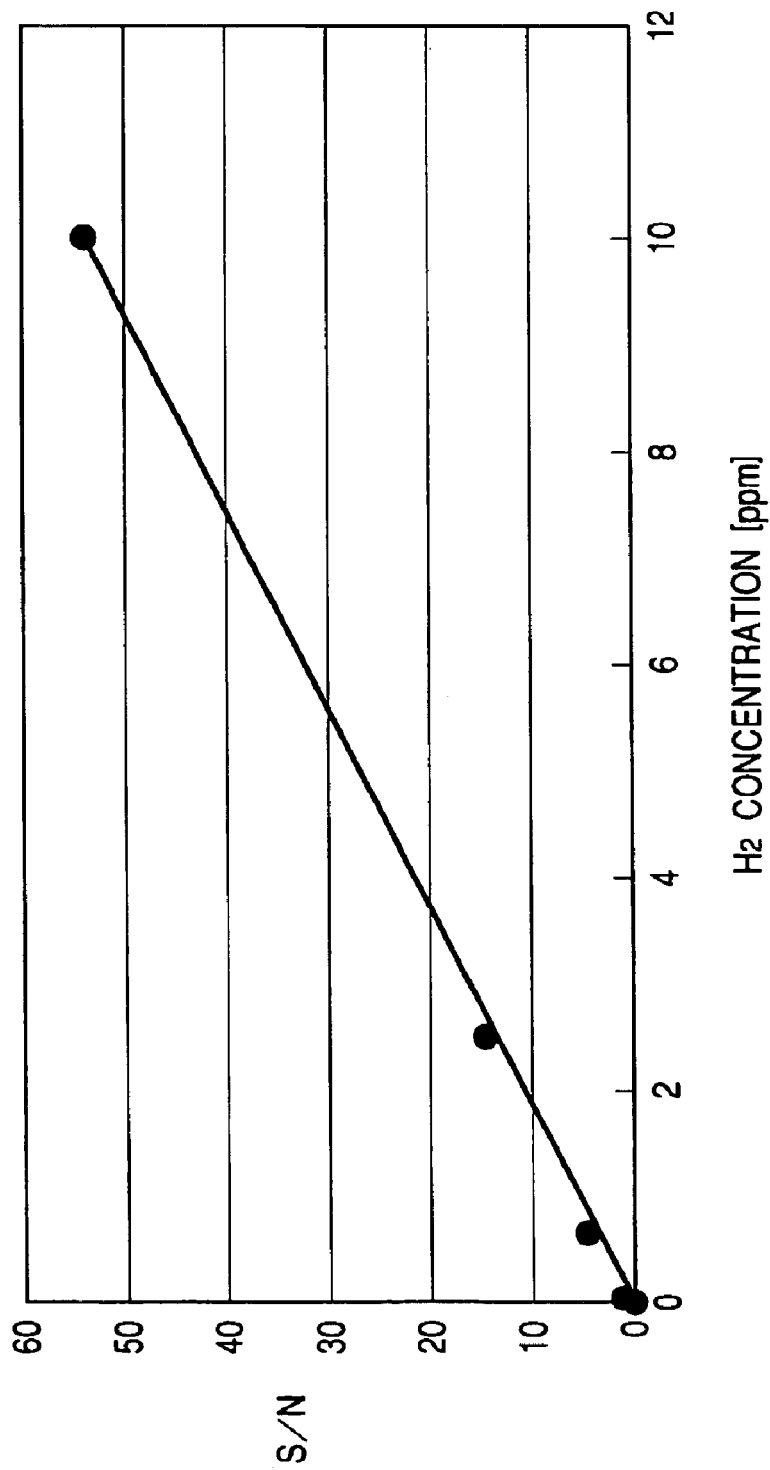
FIG. 4 is a view showing relationship between concentration of hydrogen obtained by adding traces of hydrogen to air in various concentrations for measurement and S/N in an example of the present invention.

FIG. 4 is a view showing relationship between concentration of hydrogen obtained by adding traces of hydrogen to air in various concentrations for measurement and S/N in an example of the present invention. The ordinate of FIG. 4 indicates a ratio (S/N) of noise N to signal intensity S of $N_2H^+$ (mass number m/z=29) ion. The result shown in FIG. 4 is a result obtained by measuring assuming a flow rate of the sample gas to be 1 L/min, and shows that hydrogen concentration can be measured at a limit of detection (S/N=3) of 0.5 ppm at high sensitivity.

Figure 5:
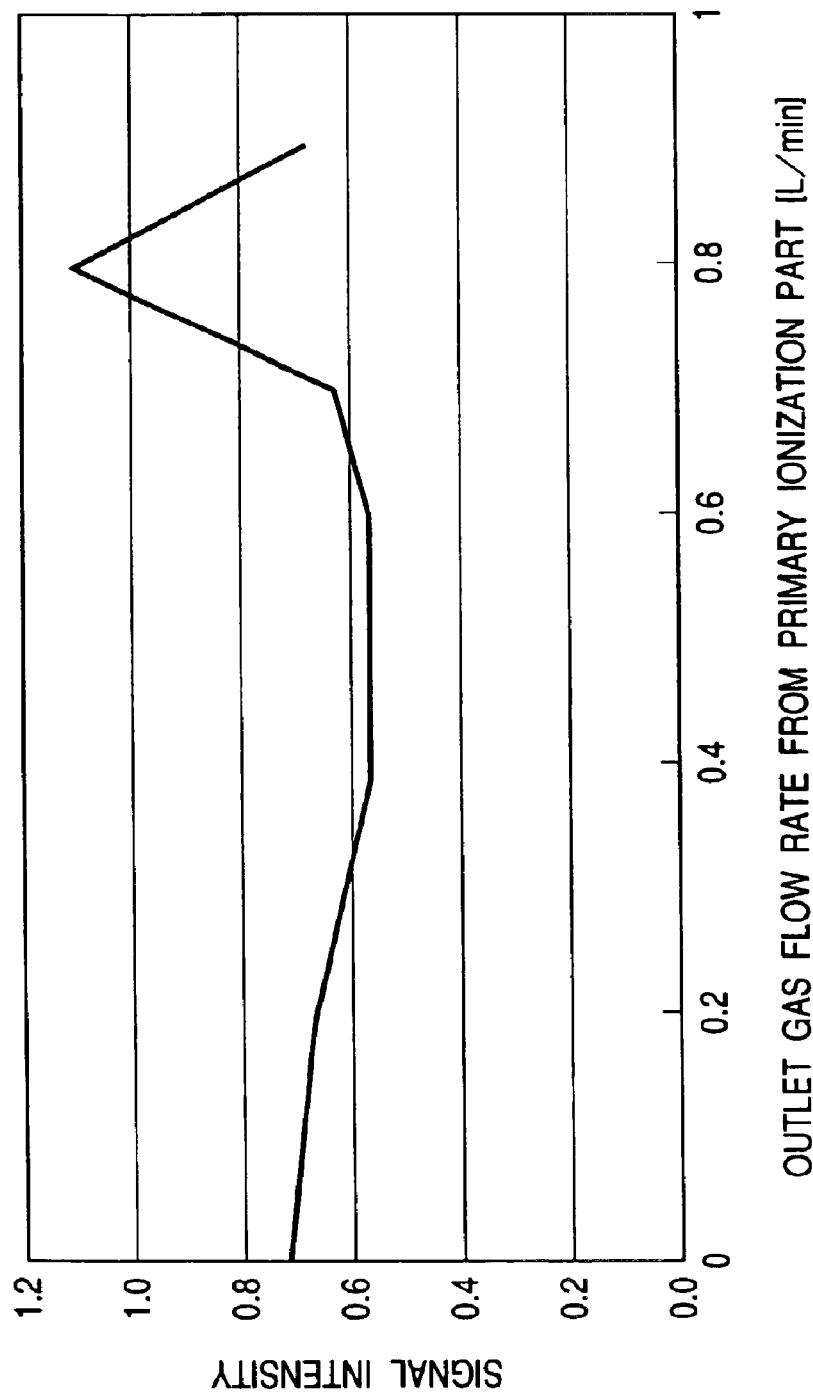
FIG. 5 is a view showing relationship between a flow rate of gas to be discharged from the primary ionization part and sensitivity in the example of the present invention.

FIG. 5 is a view showing relationship between a flow rate of gas to be discharged from the primary ionization part and sensitivity in the example of the present invention, and shows signal intensity of $N_2H^+$ (mass number m/z=29) ion measured when air added with 2.5 ppm of hydrogen is used as the sample gas in a case where argon gas is introduced into the primary ionization part 28 as reagent gas and a flow rate of argon gas to be discharged from the reagent gas outlet piping 17 is controlled and changed by the mass flow controller 20.

FIG. 5 shows a result obtained by measuring when 1 L/min of argon gas is introduced into the primary ionization part 28 and 1 L/min of the sample gas is introduced into the secondary ionization part 23. When a flow rate of the argon gas to be discharged is up to 0.6 L/min, signal intensity of the ion gradually decreases; in the neighborhood of 0.7 L/min, the signal intensity of the ion is increased; and in the neighborhood of 0.8 L/min, it has a peak. When the flow rate of the argon gas to be discharged is 0.8 L/min, the flow rate of argon gas which passes through a hole of the counter electrode 22 together with the primary ion $Ar^+$ is (1−0.8) L/min=0.2 L/min.

This shows that when an amount of gas which flows through the hole of the counter electrode 22 is too large, an influence of the sample gas being diluted in the secondary ionization part 23 becomes large to decrease the sensitivity, while when too small, it becomes difficult for the primary ion to be stably supplied to the secondary ionization part 23 through the hole of the counter electrode 22 and an efficiency of the secondary ionization in the secondary ionization part 23 will be decreased. Therefore, an adequate amount of gas for generating the primary ion when passing through the hole of the counter electrode 22 is (0.1 to 0.3) L/min.

Figure 6:
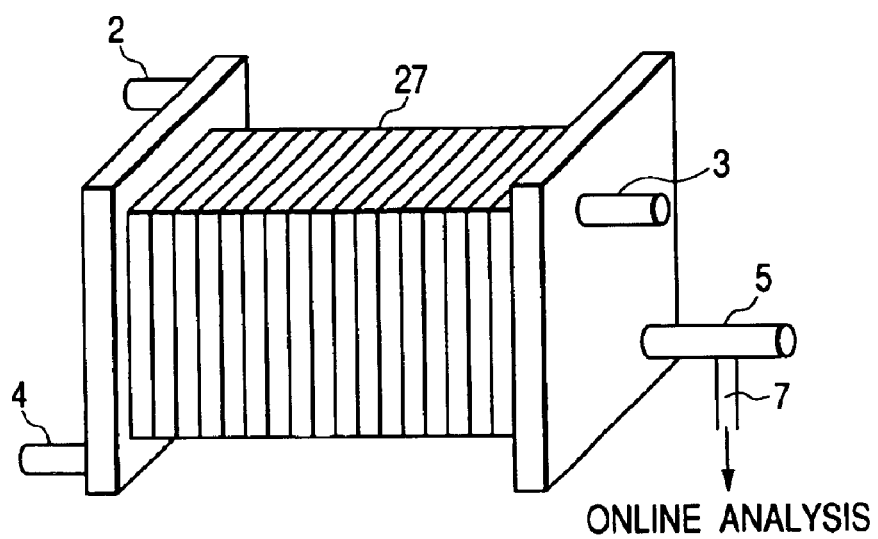
FIG. 6 is a view for explaining structure in which there is performed an online analysis of outlet gas from a fuel cell obtained by stacking a plurality of fuel cells as a single unit in the example of the present invention.

FIG. 6 is a view for explaining structure in which there is performed an online analysis of outlet gas from a fuel cell obtained by stacking a plurality of fuel cells as a single unit shown in FIGS. 1, 3 as a stack in the example of the present invention. In FIG. 6, the structure of the branch 6 to the mass spectrometric part 11 shown in FIG. 1 has been omitted. As shown in FIG. 6, it is possible to measure by connecting the gas piping to the mass spectrometer so as to branch it as in the case of FIG. 1, and it is possible to inspect for any defective fuel cell by measuring an amount of leak as the entire fuel cell stack 27 online.

In the foregoing description, the description has been made of structure and method for measuring the crossover leak by sampling gas in the gas outlet piping 5 on cathode, and through the use of the similar structure and method thereto, there is provided the branch 6 in the gas inlet piping 2 on anode, the gas inlet piping 3 on cathode, the gas outlet piping 4 on anode, and the sample gas inlet piping 7 is connected to the branch 6, whereby gas in these piping 2, 3, 4 can be sampled for analysis. Particularly, in the case of the DMFC, methanol and water content are supplied to the anode side as fuel. When measuring formic acid and formaldehyde which are intermediate products, in the sample gas inlet piping 7 to be connected to the branch 6 to be provided in the gas outlet piping 4 on cathode, there flows a liquid intermediate product. The sample gas inlet piping 7 to the mass spectrometer is heated to vaporize the intermediate product, and it can be led to the mass spectrometer 8 for measurement.

As described above, not only detection of the crossover leak of the fuel cell, but also detection of impurity in the gas to be introduced into the fuel cell on the anode and cathode sides, and impurity in the gas to be exhausted from the fuel cell on the anode side can be performed at high sensitivity online without disturbing the operating system of the fuel cell in a state in which the fuel cell has been operated.

In the mass spectrometer according to the present invention, since traces of leak gas in the outlet gas of the fuel cell can be measured in a low limit of detection at high sensitivity, it is possible to construct a fuel cell inspection system for monitoring deterioration and defects in an electrolyte membrane online in an inspection process in the manufacture of the fuel cell. The electrolyte membrane is an important component element for affecting the performance, durability and service life of the fuel cell.

In the present invention, it is possible to measure at high speed by introducing inlet gas and outlet gas of the fuel cell sampled directly or after mixing with dilution gas into the atmospheric pressure chemical two-step ionization source in which an ion-molecule reaction is effectively performed, and ionizing highly selectively and at high sensitivity for analysis without the need for pretreatment of the sample. Also, a flow rate of gas to be consumed for the analysis is as low as about 0.1 L/min, and it is possible to measure without disturbing the system of fuel cell.

Through the use of an inspection device using a mass spectrometer according to the present invention, an automotive fuel cell can be also inspected as below. That is, while a fuel replenishment station for fuel cells, for example, a hydrogen gas station is replenishing fuel to a fuel storage equipment, the crossover leak in the outlet gas of the fuel cell is inspected, whereby if the fuel cell is inspected, it will be possible to notify the driver of presence or absence of necessity for repair or replacement of the fuel cell. Since the inspection can be made during replenishment of fuel, there is no need for sparing excessive time for the inspection, but it is convenient for the driver.

According to the present invention, it is possible to provide a mass spectrometer capable of detecting impurity in sample gas of a low flow rate in a high sensitivity, to introduce a sample from a system targeted for inspection for analysis without disturbing the system targeted for inspection as far as possible, and to provide a mass spectrometer capable of detecting the crossover leak of the fuel cell, impurity in the inlet gas to the fuel cell, and impurity in the outlet gas from the fuel cell in a state in which the fuel cell has been operated without disturbing the operation system of the fuel cell online in a high sensitivity with the target of inspection as, for example, the fuel cell.

What is claimed is:

1. A mass spectrometer, comprising:
an atmospheric pressure chemical ionization source having a primary ionization part for generating a primary ion by means of electric discharge of a reagent gas, a secondary ionization part for generating an ion of a sample gas by a reaction of said primary ion and said sample gas, and a hole disposed between said primary ionization part and said secondary ionization part as a passage for said primary ion to enter from said primary ionization part into said secondary ionization part while said secondary ionization part being maintained at negative pressure as compared with said primary ionization part;
a mass spectrometric part for performing mass spectrometric analysis of said ion generated in said secondary ionization part;
a mixing portion for mixing said sample gas to be introduced into said secondary ionization part with a dilution gas;
means for controlling a flow rate of said dilution gas for flowing through said mixing portion; and
means for controlling a flow rate of said sample gas for flowing through said mixing portion,
wherein mixed gas obtained by mixing said sample gas with said dilution gas is introduced into said secondary ionization part.

2. The mass spectrometer according to claim 1, wherein an ionization potential of said dilution gas is the same as or higher than an ionization potential of a substance targeted for measurement in said sample gas, or proton affinity of said dilution gas is the same as or lower than that of the substance targeted for measurement in said sample gas.

3. The mass spectrometer according to claim 2, wherein said sample gas is a sample to be collected from an inlet piping for introducing gas or liquid to a fuel cell or an outlet piping for discharging gas or liquid from said fuel cell.

4. The mass spectrometer according to claim 3, wherein said regent gas for generating said primary ion is argon or helium.

5. The mass spectrometer according to claim 3, wherein an outlet flow rate of said reagent gas to said secondary ionization part is 0.1 to 0.3 L/min.

6. A mass spectrometer, comprising:
an atmospheric pressure chemical ionization source having a primary ionization part for generating a primary ion by means of electric discharge of a reagent gas, a secondary ionization part for generating an ion of a sample gas by a reaction of said primary ion and sample gas to be collected from a gas outlet piping on a cathode of a fuel cell, and a hole disposed between said primary ionization part and said secondary ionization part as a passage for said primary ion to enter from said primary ionization part into said secondary ionization part while said secondary ionization part being maintained at negative pressure as compared with said primary ionization part;
a mass spectrometric part for performing mass spectrometric analysis of said ion generated in said secondary ionization part;
a mixing portion for mixing said sample gas to be introduced into said secondary ionization part with dilution gas;
means for controlling a flow rate of said dilution gas for flowing through said mixing portion; and
means for controlling a flow rate of said sample gas for flowing through said mixing portion,
wherein said means for controlling a flow rate of said sample gas is disposed at an outlet piping of said atmospheric pressure chemical ionization source, and mixed gas obtained by mixing said sample gas with said dilution gas is introduced into said secondary ionization part, and said dilution gas is any of argon, helium and nitrogen, and hydrogen in said sample gas is detected.

7. The mass spectrometer according to claim 6, wherein a flow rate of said dilution gas for flowing through said mixing portion is higher than that of said sample gas for flowing through said mixing portion.

8. The mass spectrometer according to claim 6, wherein an outlet flow rate of said reagent gas to said secondary ionization part is 0.1 to 0.3 L/min.

9. The mass spectrometer according to claim 1, wherein said means for controlling a flow rate of said sample gas is disposed at an outlet piping of said atmospheric pressure chemical ionization source.

10. The mass spectrometer according to claim 1, wherein said reagent gas is ionized in the vicinity of an electrode and than passing through said hole arranged in a counter electrode set between said primary ionization part and said secondary ionization part.

11. The mass spectrometer according to claim 6, wherein said reagent gas is ionized in the vicinity of an electrode and than passing through said hole arranged in a counter electrode set between said primary ionization part and said secondary ionization part.

* * * * *